United States Patent
Hockey et al.

[11] Patent Number: 6,014,024
[45] Date of Patent: Jan. 11, 2000

[54] APPARATUS AND METHOD FOR DETECTING AND/OR MEASURING FLAWS IN CONDUCTIVE MATERIAL

[75] Inventors: Ronald L. Hockey; Douglas M. Riechers, both of Richland, Wash.

[73] Assignee: Battelle Memorial Institute, Richland, Wash.

[21] Appl. No.: 09/040,543

[22] Filed: Mar. 17, 1998

Related U.S. Application Data

[63] Continuation-in-part of application No. 08/691,052, Aug. 1, 1996, Pat. No. 5,777,469, which is a continuation-in-part of application No. 08/509,551, Jul. 31, 1995, abandoned.

[51] Int. Cl.⁷ .............................. G01N 27/82; G01R 33/12
[52] U.S. Cl. .......................................... 324/240; 324/225
[58] Field of Search .................................. 324/240, 241, 324/219, 220, 239, 242, 243, 226, 225

[56] References Cited

U.S. PATENT DOCUMENTS

| | | | |
|---|---|---|---|
| 2,519,367 | 8/1950 | Gunn et al. | 324/240 |
| 2,970,256 | 1/1961 | Sazyhski et al. | 324/240 |
| 3,881,151 | 4/1975 | Bigelow | 324/226 |

*Primary Examiner*—Walter E. Snow
*Attorney, Agent, or Firm*—Paul W. Zimmerman

[57] ABSTRACT

The present invention uses a magnet and sensor coil unilaterial and in relative motion to a conductive material, to measure perturbation or variation in the magnetic field in the presence of a flaw. A liftoff compensator measures a distance between the conductive material and the magnet.

28 Claims, 11 Drawing Sheets

⊙ CURRENT FLOW OUT OF PAGE
⊗ CURRENT FLOW INTO PAGE

DIAGRAM OF HOLES AND NOTCHES IN THICK STEEL DISK

| FLAW NUMBER | THROUGH-WALL HOLE | PERCENT THROUGH-WALL 0.02 INCH DIA. HOLE | 0.02" WIDE NOTCH |
|---|---|---|---|
| 1 | 0.06 INCH DIAMETER | | |
| 2 | 0.052 INCH DIAMETER | | |
| 3 | 0.04 INCH DIAMETER | | |
| 4 | 0.031 INCH DIAMETER | | |
| 5 | 0.02 INCH DIAMETER | | |
| 6 | | 50 (SAME SIDE) | |
| 7 | | 25 (SAME SIDE) | |
| 8 | | 50 (OPPOSITE SIDE) | |
| 9 | | 25 (OPPOSITE SIDE) | |
| 10 | | | 0.01 DEEP |
| 11 | 0.02 INCH DIAMTER | | |

SLOTS ARE 0.031" INCH LONG BY 0.050 INCH WIDE

1. @ 123° SLOT 0.020" DEEP
2. @ 142° SLOT 0.040" DEEP
3. @ 161° SLOT 0.080" DEEP
4. @ 180° SLOT THRU DISK
5. @ 218° HOLE 0.020" DIAMETER
6. @ 231° HOLE 0.031" DIAMETER
7. @ 244° HOLE 0.040" DIAMETER
8. @ 257° HOLE 0.052" DIAMETER
9. @ 270° HOLE 0.060" DIAMETER

10 INCH DIAMETER ALUMINUM DISK, 0.125 INCH THICK

APPARATUS AND METHOD FOR DETECTING AND/OR MEASURING FLAWS IN CONDUCTIVE MATERIAL

CROSS REFERENCE TO RELATED INVENTIONS

This application is a continuation-in-part of application Ser. No. 08/691,052 filed Aug. 01, 1996 now U.S. Pat. No. 5,777,469 which is a continuation-in-part of application Ser. No. 08/509,551 filed Jul. 31, 1995, now abandoned.

FIELD OF THE INVENTION

The present invention relates generally to a method and apparatus for detecting and/or measuring flaws in conductive material. More specifically, the present invention uses a magnet and sensing coil both in oscillatory motion with respect to a conductive material, to measure perturbation or variation in the magnetic field in the presence of an inclusion. As used herein, the term "conductive" means electrically conductive. Also, as used herein, the term "flaw" means defect, inclusion, especially non-metallic inclusion, crack or other electrical conductivity discontinuity. The terms "oscillatory" and "oscillating" are interchangeable and include both linear oscillation and non-linear (e.g. circular) oscillation motion.

BACKGROUND OF THE INVENTION

Inspection of parts for determination of maintenance needs is important, especially for products having a narrow margin of safety and/or having high safety requirements as in the aircraft industry. Identifying flaws, fatigue cracks and other material discontinuities in an aircraft skin is critical to aircraft performance, reliability and safety. Present inspection is visual by a trained technician, or inspector, with or without disassembly.

U.S. Pat. No. 3,881,151 uses an invariant magnetic field gradient and sensor for detection of flaws in moving electrically conductive objects such as tube, bar, wire, and wire rods. Detectable flaws include laps, cuts, seams and entrapped foreign materials. However, the '151 patent requires a magnetic field gradient and requires that the conductive material to be inspected be passed through a hollow cylindrical magnet. It further requires two sensors for flaw detection.

Figure 1:
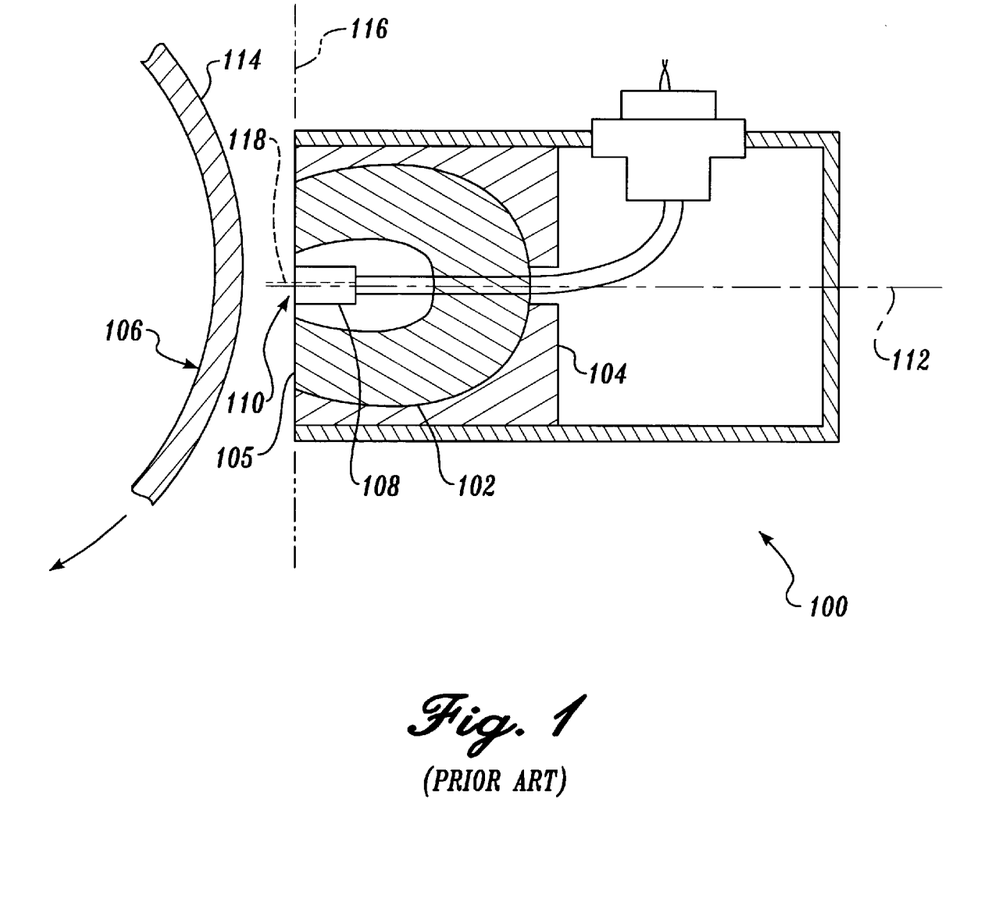
FIG. 1 shows a prior art sensing unit.

U.S. Pat. No. 2,519,367 to Gunn et al. is for a method and apparatus for detecting defects in objects as depicted in FIG. 1 (prior art). The apparatus or sensing unit 100 has a horseshoe magnet 102 embedded in insulating material 104 with the feet 105 of the horseshoe magnet exposed and placed adjacent to one side of the conductive material 106 to be inspected. A single sensing coil 108 is positioned between the legs of the horseshoe magnet 102 and is stationary with respect to the horseshoe magnet 102 by embedment within the insulating material 104 and is also placed adjacent the conductive material 106. Both the magnet 102 and sensing coil 108 are stationary while the conductive material 106 is moved past them. An oscilloscope (not shown) connected to the sensing coil 108 receives a signal from the sensing coil 108 when a flaw (not shown) in the conductive material 106 passes by the apparatus 100.

The magnet 102 has a datum point 110 that is a point located on a center line 112 through a center of the magnet and substantially perpendicular to a material surface 114 and on a plane 116 defined by magnet surface(s) (feet 105) facing the material surface 114. The sensing coil 108 has a datum orientation with a longitudinal axis 118 of the sensing coil 108 substantially perpendicular to the material surface 114. In the prior art embodiment of FIG. 1, center line 112 and longitudinal axis 118 are co-linear. They are shown side by side in FIG. 1 for clarity.

Disadvantages of the prior art include (1) require motion of the part to be inspected, (2) limited flaw size detection for flaws having a volume below about 1 mm$^3$, (3) inability to detect subsurface flaws, and (4) inability to quantify flaw area or volume. Distance of the sensing coil 108 from the surface or part to be inspected is not discussed, especially for the application of inspecting planar surfaces.

SUMMARY OF THE INVENTION

The present invention is an improved sensing unit wherein the sensor coil is placed with its longitudinal axis parallel to the surface of the part. In addition, the sensor coil and magnet are unilateral with respect to the part to be inspected, and they are in an oscillatory motion with respect to the part to be inspected.

The inspected part is substantially stationary with respect to the oscillatory motion. This is because in a practical application, for example aircraft skin inspection, it is simply not practical to move the wing fast enough to induce sufficient eddy current to effect a measurement. Either the wing or the sensing unit may be moved to accomplish inspection at different locations on the conductive material. Moving the wing is not as practical as moving the sensing unit.

Further, the sensor coil is positioned in an optimum position corresponding to the highest sensor coil output signal that is obtained from a secondary magnetic field in a position that is substantially free of effects from a primary magnetic field. The primary magnetic field is that of the magnet, and the secondary magnetic field is that of the induced eddy current within the conductive material produced by the oscillating motion of the magnet relative to the conductive material.

Position of the sensor coil in the optimum position increases sensitivity for detecting flaws having a characteristic volume less than about 1 mm$^3$, and further permits detection of subsurface flaws. Use of multiple sensor coils permits quantification of flaw area or volume, and makes statistical methods of detection more convenient.

In a practical conductive material, for example an aircraft skin, there are surface geometry variations, including but not limited to dents, dimples, sag, paint thickness variation, and combinations thereof that would cause a variation in liftoff distance between the surface of the conductive material and the oscillating magnet. Such variation in liftoff distance introduces error into the sensor coil signal. According to the present invention, a liftoff compensator is included that measures the actual liftoff distance during inspection scans, thereby enabling correction/normalization of the raw sensor coil signal.

It is an object of the present invention to provide an apparatus for inspecting and quantifying flaw size in conductive material of a substantially non-moving or stationary part.

It is a yet further object of the present invention to provide an apparatus for detecting subsurface flaws in conductive material or conductive material layers, wherein the apparatus is fully positioned on one side of the conductive material.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 5b is a detail of the sensing unit in FIG. 5a.

DESCRIPTION OF THE PREFERRED EMBODIMENT(S) APPARATUS

The apparatus of the present invention is a sensing unit for detecting flaws in conductive material, wherein the sensing unit is a combination of a magnet and sensor coil in unilateral relationship to a conductive material, and the sensing unit is in oscillatory motion with respect to the conductive material. The conductive material is substantially stationary compared to the rate of oscillation. Either the sensing unit or the conductive material may be moved to perform flaw detection at various locations of the conductive material. Oscillatory motion may be geometrically linear or non-linear. Geometric linear oscillatory motion is reciprocating motion or back-and-forth along a line. Geometric non-linear oscillating motion includes but is not limited to circular motion.

The sensor coil is positioned with respect to the magnet in an optimum position corresponding to the highest sensor coil output signal that is obtained from a secondary magnetic field Bs in a position that is substantially free of effects from a primary magnetic field Bp. The primary magnetic field is that of the magnet, and the secondary magnetic field is that of the induced eddy current within the conductive material produced by the oscillating motion of the magnet relative to the conductive material. Position of the sensor coil in the optimum position increases sensitivity for detecting flaws having a characteristic volume less than about 1 mm$^3$, and further permits detection of subsurface flaws by maximizing the ratio of Bs/Bp. Use of multiple sensor coils permits quantification of flaw area or volume, and facilitates use of statistical methods for detection.

Figure 2A:
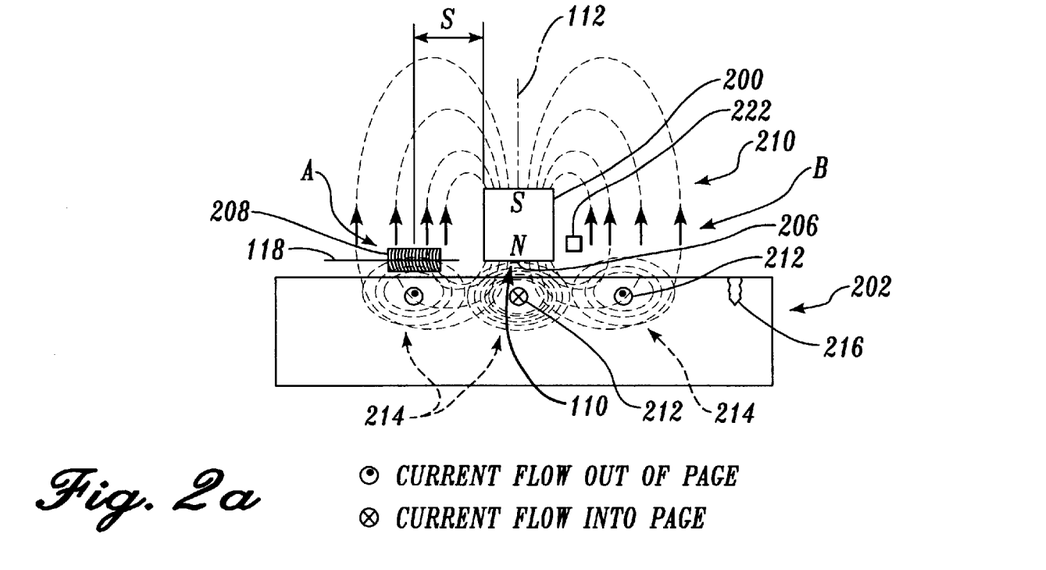
FIG. 2a shows an embodiment of a sensing unit in accordance with the present invention.

In FIG. 2a, the sensing unit has a magnet 200 having a substantially constant magnetic field, that is placed adjacent to one side of the conductive material 202. The magnet 200 has a datum point 110 defined by an intersection of (1) a center line 112 through a center of the magnet 200 and perpendicular to the material surface 204 with (2) a plane 116 defined by a magnet surface(s) 206 facing the material surface 204. The apparatus further has a sensor coil 208 that is stationary with respect to the magnet 200 wherein the magnet 200 and sensor coil 208 are in oscillatory motion with respect to the conductive material 202. With the magnet 260 and sensor coil 208 mounted on a rotating disk, the oscillatory motion is circular. When the magnet 200 and sensor coil 208 are mounted on a linear oscillating platform, the relative motion is reciprocating or vibratory. The sensor coil 208 has a longitudinal axis 118 defining an orientation of the sensor coil 208. The oscillatory motion may be adjustable. Preferably, the spacing between the magnet 200 and the sensor coil 208 may be adjustable between measurement scans.

The present invention is an improvement wherein the sensor coil 208 is positioned away from the datum point 110. FIG. 2a shows the magnet 200 with its pole 206 facing the conductive material 202 and the magnet's primary magnetic field (Bp) 210 extending from the magnet 200 to and through the conductive material 202. With oscillatory motion of the magnet 200 in relation to the conductive material 202, an eddy current 212 is induced in the conductive material 202. The eddy current 212 generates a secondary magnetic field (Bs) 214. Because the eddy current 212 induced by the primary magnetic field 210 is continuous within the conductive material 202, and the generated secondary magnetic field 214 is also continuous in a toroidal shape centered about the eddy current 212, the sensor coil 208 may be positioned anywhere within the toroidal shape of the secondary magnetic field 214.

Although the secondary magnetic field 212 is strongest beneath the magnet 200 at the datum point 110, the primary magnetic field 210 is also quite strong in that location that can magnetically saturate a core or approach a magnetic saturation within the sensor coil 208. Because the secondary magnetic field is continuous in a circular pattern, the sensor coil 208 may be located in any position within the circular pattern. The primary magnetic field diminishes in strength further from the magnet. Thus, by placing the sensor coil 208 within the circular pattern of the secondary magnetic field 214 at a distance away from the magnet 200, sufficient signal is received stronger than any competing signal from the primary magnetic field 210 thereby permitting detection of a flaw 216. Thus, The sensor coil 208 is placed at a spacing or distance S from the magnet 200 to intersect a concentration of magnetic field lines of the secondary magnetic field 214. For the magnet 200 and sensor coil 208 in unilateral relationship as shown, the spacing S will be within a magnet dimension from the rear face of the magnet 200, preferably within about a ½ magnet dimension. In other words, the sensor coil 208 is shown in antidatum location away from the datum point 110. The first antidatum location A is unilateral or on the same side of the conductive material 202 and displaced from the centerline 112.

Because the secondary magnetic fields also are present "ahead" of the magnet in position B, the sensor coil 208 may be placed ahead of the magnet 200. Alternatively, one may place sensor coils 208 ahead (A) and behind (B) the magnet in applications where a dual signal may improve reliability of flaw detection. In a unilateral position, it is observed that when the relative motion between the conductive material 202 and the sensing unit is in a direction V wherein the magnet 200 "sees" new conductive material 202 ahead of the sensor coil 208, the phase of sensor current is opposite that of the relationship wherein the sensor coil "sees" new conductive material 202 ahead of the magnet.

Figure 2B:
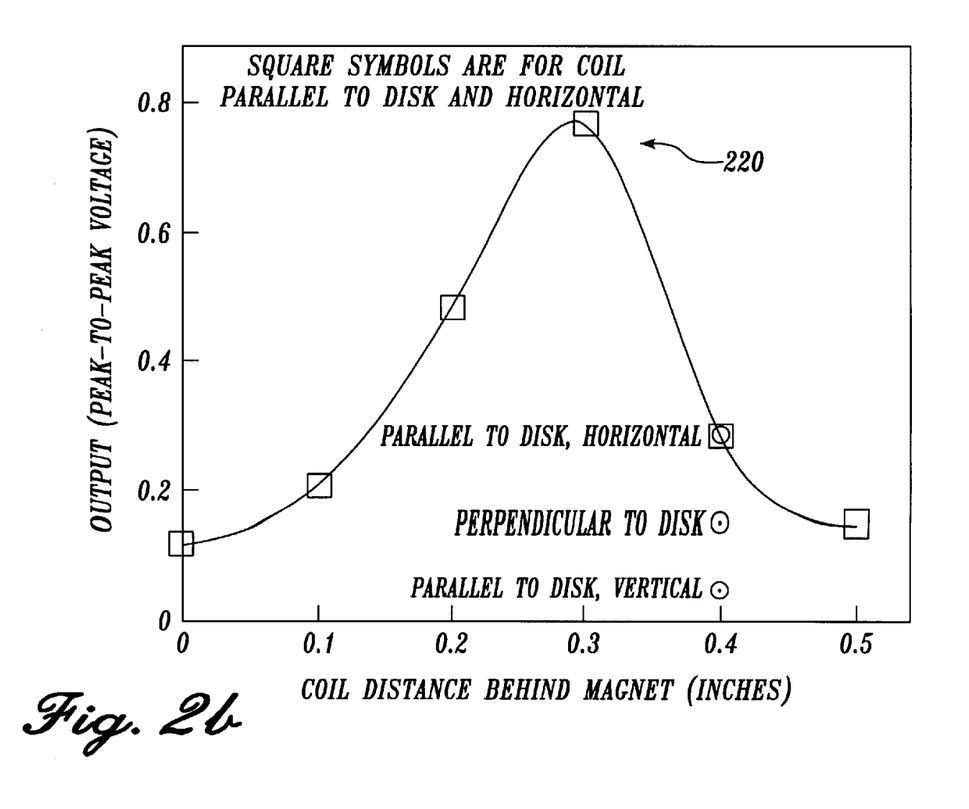
FIG. 2b is a graph of sensor coil output versus spacing between the magnet and the sensor coil.

The spacing or distance between the magnet 200 and sensor coil 208 depends upon the field strength and physical size of the magnet 200, and the sensitivity and size of the sensor coil 208. Nevertheless, for a given sensing unit, there is a spacing that gives a maximum signal from the sensor coil 208. FIG. 2b is a graph of the relationship between signal strength and spacing. The spacing corresponding to the peak 220 is the optimum spacing. The data in FIG. 2b were obtained with a cubic shaped magnet 0.5 inch on a side.

Having the magnet 200 and the sensor coil 208 unilateral permits detection of flaws in structures that are not accessible on both sides.

The liftoff distance D of the sensor coil 208 from the conductive material 202 is not critical so long as the liftoff distance D is constant, but the sensor coil 208 must be within the induced magnetic field 214. It was observed that the induced current in the coil from a flaw 216 is increased as the liftoff distance D is decreased. Hence, it is preferred to place the sensor coil 208 as near the conductive material 202 as possible.

Where there are variations in the surface geometry of a conductive material 202, it is necessary to characterize those variations in order to correct or normalize the signal from the sensor coil 208. A liftoff compensator may be an electronic or optical distance sensor. An optical sensor with shorter response time may be preferred for higher speed oscillation. An electronic distance sensor may be, for example, a Hall effect sensor, eddy current coil, or linear variable displacement transformer (LVDT).

Figure 3A:
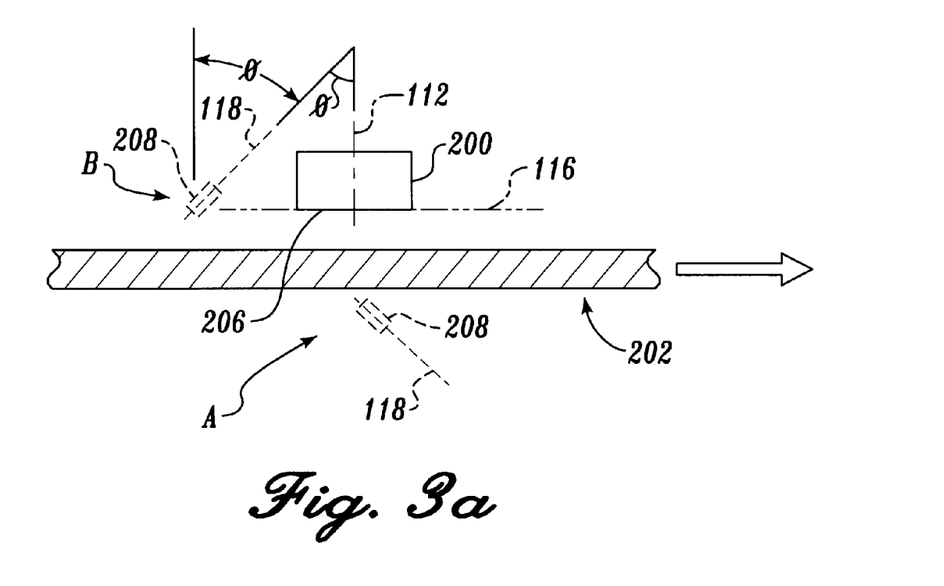
FIG. 3a shows a tilted sensor embodiment of a sensing unit in accordance with the present invention.

According to another aspect of the present invention, additional flaw detection sensitivity is achieved by orienting the sensor 208 parallel to the surface of the conductive material 202. In FIG. 2a, the sensor coil 208 is in the preferred orientation with its longitudinal axis 118 perpendicular to the center line 112. FIG. 3a shows the sensor 208 tilted from the datum orientation with the longitudinal axis 118 antiparallel with respect to the center line 112.

Figure 3B:
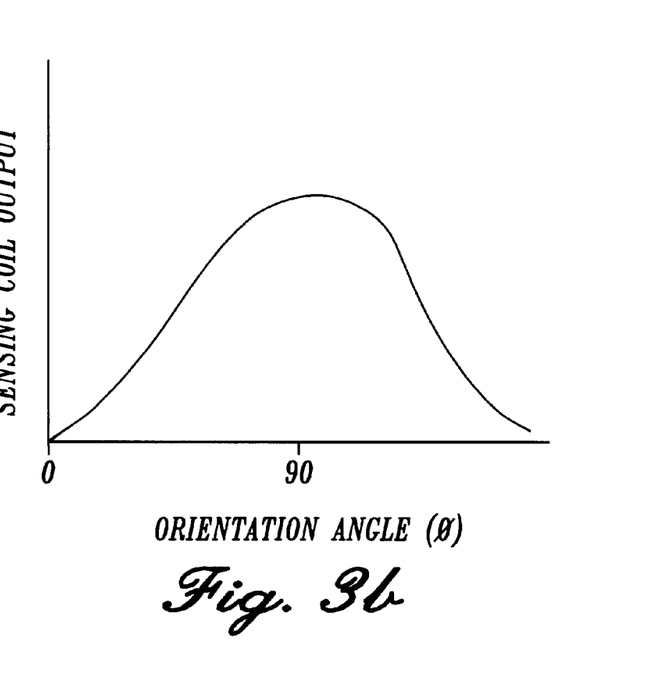
FIG. 3b is a graph of sensor coil output versus orientation angle of the sensor coil.

FIG. 3b shows a graph of signal strength as a function of orientation angle phi. The maximum signal strength is achieved with the sensor coil 208 substantially parallel to the conductive material 202 and substantially perpendicular to the center line 112.

In operation, as the magnet and sensor coil are oscillated and the conductive material 202 is consistent, no signal is produced in the sensor coil 208 because the secondary magnetic field 214 is constant. However, upon appearance of a flaw 216, there is an interruption in the primary magnetic field 210, which imparts a change to the eddy current 212 and thence a change in the secondary magnetic field 214. Upon a change in the secondary magnetic field 214, a signal voltage current is induced in the sensor coil 208 which is proportional to the size of the flaw.

Figure 5:
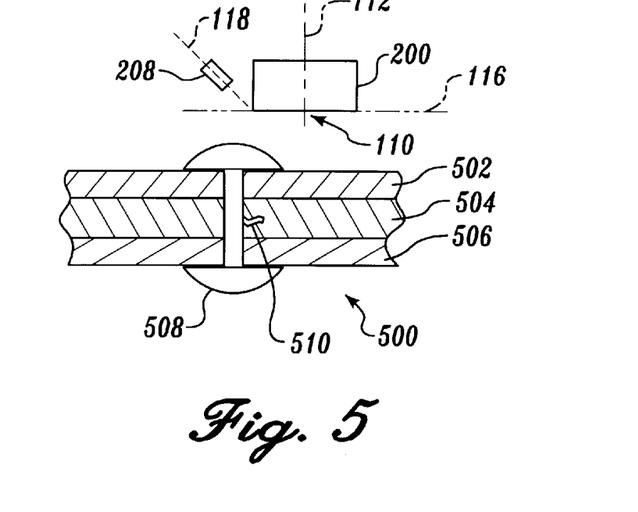
FIG. 5 shows an internal flaw in an assembly of three layers of conductive material held by a rivet.

In particular, aircraft wings are laminate structures held together with rivets. The advent of the present invention makes it possible to inspect the riveted connections of the wings. Aircraft wing inspection is illustrated in FIG. 5. A multi-layered metallic structure 500, for example a wing section, has three layers 502, 504, 506 held together by a rivet 508. A magnet 200 in combination with a sensor coil 208 in a unilateral antidatum relationship are used to detect the flaw 510. Flaw 510 is a subsurface flaw that is generally not detectable by a sensing unit. However, the increased sensitivity of the present invention non-datum positioning or orientation permits detection of subsurface flaws.

Figure 4:
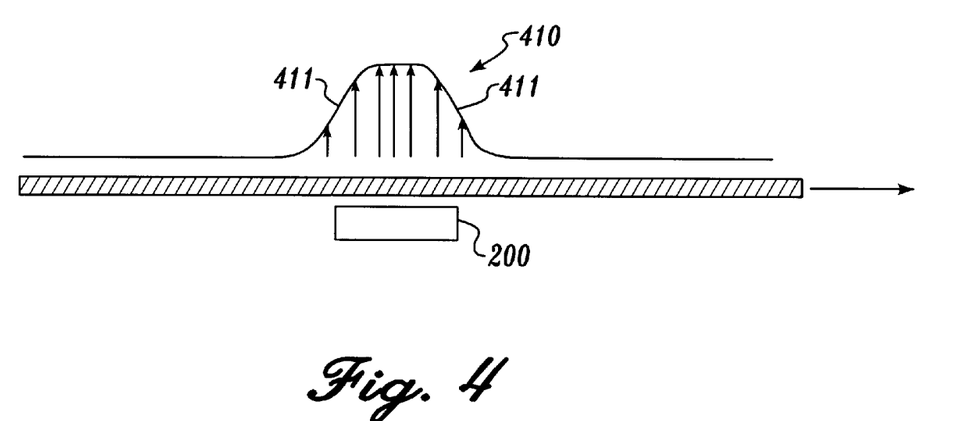
FIG. 4 shows a magnetic field.

The magnet 200 may be any type of electromagnet or permanent magnet. It is preferred that the magnet 200 be a neodymium 27 permanent magnet because of it's high magnetic flux density. The magnet 200 may be of any cross section and any size. It is preferred that the magnet 200 have a substantially square cross section and have a size of less than about 1 inch on a side, preferably less than about ½ inch on a side. FIG. 4 illustrates a substantially constant magnetic field 410. Edge gradients 411 are a result of edge effects, but are not relied upon for measurements nor do they hinder measurements of flaws.

The sensor coil 208 is simply a coil of a conducting material. It is preferred to use copper wire for the coil of conducting material. It is further preferred that the sensor coil 208 be of a size compatible with the size of flaw to be detected. For example detection of a flaw having a dimension of 0.020 inch is preferably done with a sensor coil of about 0.020 inches in length. The coil signal may be increased by inclusion of a conductive core, preferably ferrite. A coil of 0.020 inches may be made with five windings of 0.001 inch diameter copper wire. For purposes of signal strength, the sensor coil should be larger, but for purposes of detecting small inclusions, the sensor coil should be smaller. Hence, one skilled in the art of flaw detection will select a sensor coil size by trading off the benefits of signal strength and inclusion size limit. It is possible to detect very small (0.001 inch) inclusions with a 0.020 inch sensor coil. However, the signal to noise ratio diminishes with coil size making it more difficult to separate the signal from the noise. However, noise can be reduced by making multiple passes of the flaw past the sensing unit. Because the noise is random, and the flaw signal is repetitive, multiple passes may be used to discern the flaw signal. This repetitive technique is referred to as "stacking". Moreover, optimal orientation of the sensor coil 208 increases the flaw signal strength. Increasing the number of turns also improves signal strength 7–8 layers of about 100 turns provides a factor of 5 increase in signal.

Signals from the sensor coil may be small. Accordingly, a buffer and amplifier may be used to increase the signal strength prior to entering the data acquisition system.

Figure 5A:
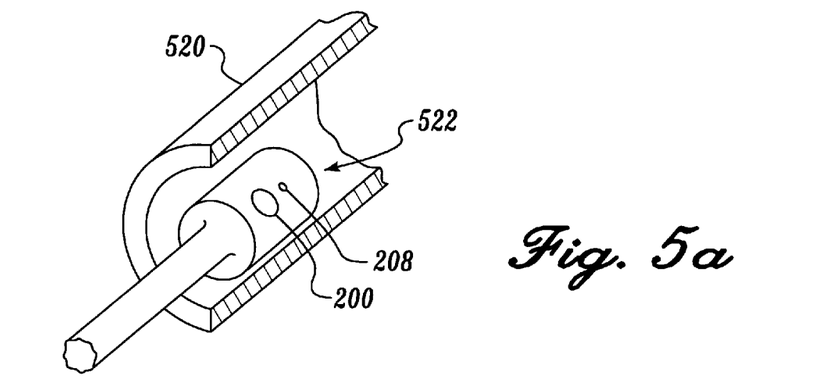
FIG. 5a shows a sensing unit useful for inspecting hollow cylinders.
Figure 5B:
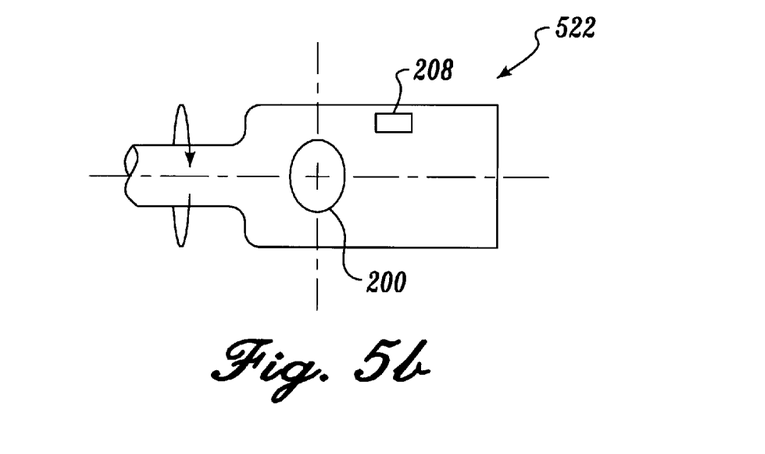

A further embodiment of the present invention is shown in FIG. 5a for inspecting a tube 520. A spindle 522 containing a magnet 200 and a sensor coil 208 in a unilateral antidatum relationship constitutes a sensing unit. The sensing unit is rotated and may also be advanced longitudinally through the tube 520. It is preferred that the sensor coil 208 be "behind" the magnet 200 with respect to the direction of rotation of the spindle 522 as shown in FIG. 5b. It is further preferred that the sensor coil 208 be oriented parallel to the pipe surface as depicted in FIG. 5b.

METHOD

The method of the present invention has the steps of placing a magnet 200 having a substantially constant magnetic field adjacent to one side of a conductive material 202, placing at least a single sensor coil 208 that is stationary with respect to the magnet 200 and on the same side of the conductive material 202 as the magnet 200, wherein the magnet 200 and sensor coil 208 are in relative motion with respect to the conductive material 202, connecting the sensor coil 208 to a data acquisition system for receiving a signal from the sensor coil 208 when a flaw in the conductive material passes by the magnet 200, and measuring a liftoff distance between the conductive material 202 and the magnet 200. Liftoff distance is measured dynamically while the relative motion continues, and is measured frequently.

In operation, a magnet 200 and sensor coil 208 are oscillated while the conductive material 202 is substantially stationary. When a flaw or inclusion passes by the magnet 200, the magnetic field is perturbed thereby inducing a signal in the sensor coil 208. The signal is measured as a voltage by a data acquisition system.

EXAMPLE 1

An experiment was conducted to demonstrate operation of the present invention. A one inch square neodymium 27 magnet with a 0.020 inch sensor coil were used in an antilateral relationship as the sensing unit according to the present invention. The signal from the sensor coil produced a signal to noise ratio of about 5 for the smallest hole on the side of the disk opposite of the magnet.

A table saw was fitted with a metal disc (without teeth). Flaws were simulated with drilled holes and/or slots in the metal disc. The metal disc rotated at about 3780 rpm resulting in a linear speed at 4.5 inch from center of about 8,900 feet per minute. Application of the magnetic field slowed the disc speed.

As the metal disc was rotated, the sensing unit was moved radially from the center of the rotating disc to the perimeter of the rotating disc. Accordingly, each flaw passed the sensing unit a plurality of times each time generating a signal. The plurality of signals for each flaw were used to quantify the area and/or volume of the flaw.

Inclusions were simulated with holes drilled in the disc of 0.020 inch diameter and depths from 25% to 100% (through) of the thickness of the disc.

EXAMPLE 2

Figure 6:
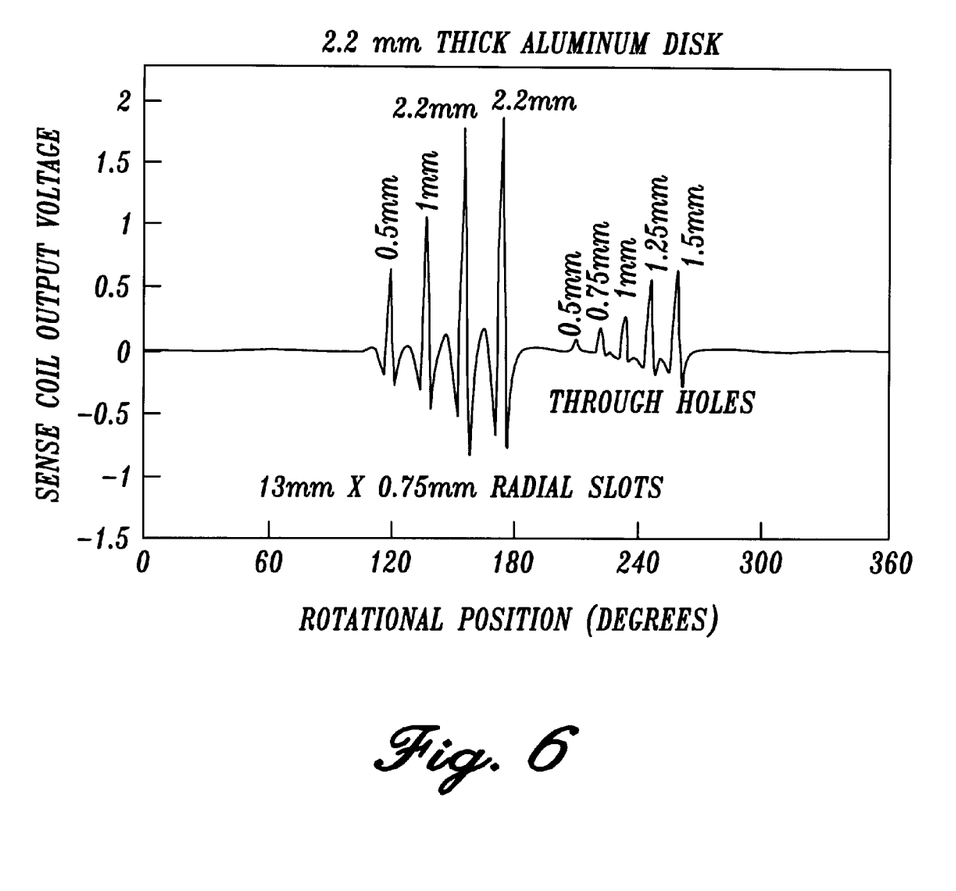
FIG. 6 is a graph of sensor coil voltage for radial slot and circular hole simulated inclusions.

Experimental apparatus as described in Example 1 was used for further testing with a 2.2 mm thick aluminum disc in accordance with the present invention. Through holes of diameters of 0.5 mm, 0.75 mm, 1 mm, 1.25 mm, and 1.5 mm were drilled to simulate inclusions. Also radial slots of 13 mm length by 0.75 mm width having depths of 0.5 mm, 1 mm, 2 mm, and 2.2 mm (through) were used. Sensor coil voltage for these inclusions are shown in FIG. 6.

EXAMPLE 3

Apparatus as described in Example 1 was further used with a steel disk prepared with simulated flaws as listed in Table E3.

Figure 7A:
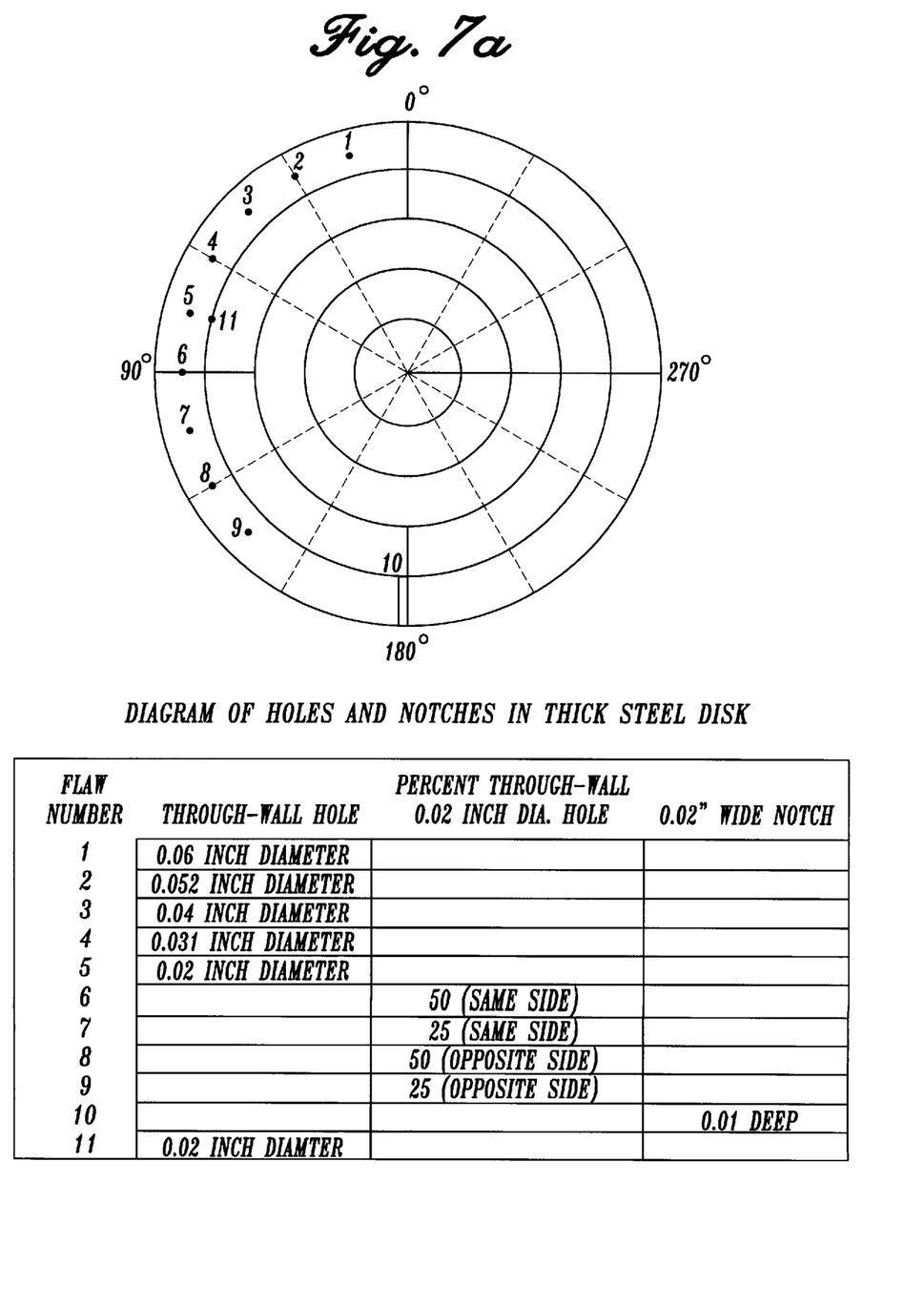
FIG. 7a is a flaw map for a steel disc.
Figure 7B:
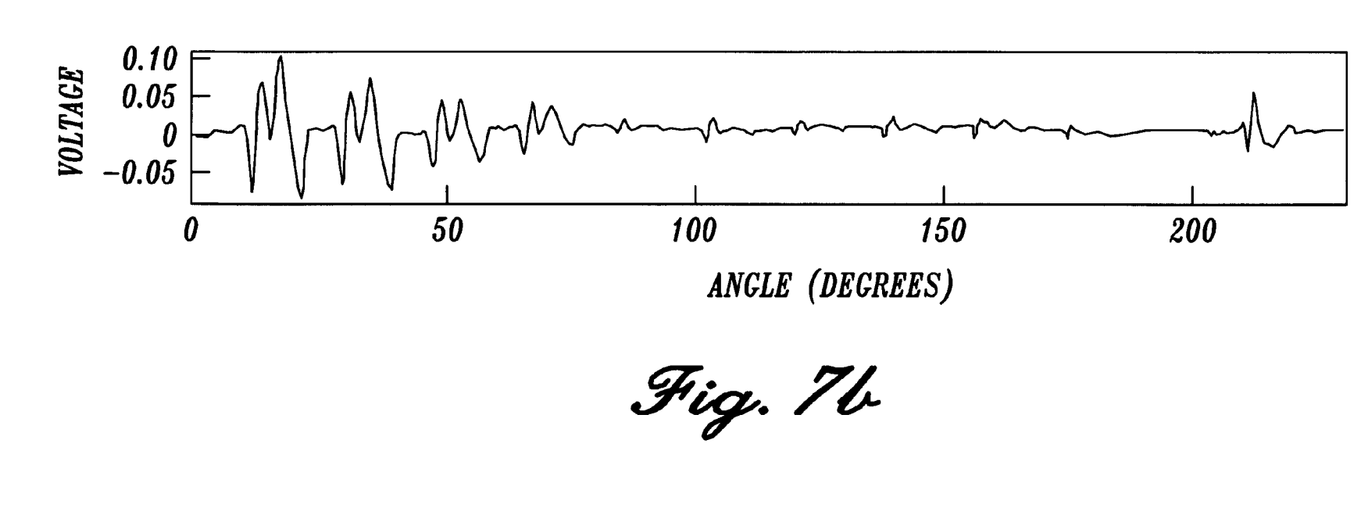
FIG. 7b is a sensor coil output for the flaws on the steel disc.
Figure 7C:
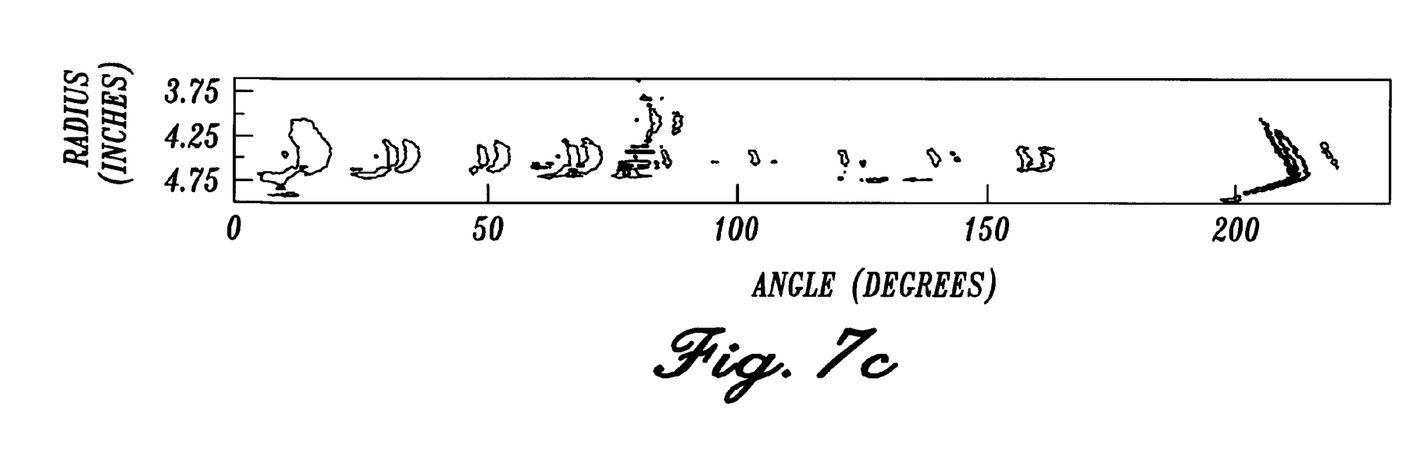
FIG. 7c is a contour plot of the flaws on the steel disc.

A flaw map is shown in FIG. 7a. Sensor coil voltages are shown in FIG. 7b with flaw cross section contours shown in FIG. 7c.

TABLE E3

Simulated Flaw Characterization

| Flaw | Through Hole Diameter (mm) | 0.5 mm Hole Percent Through | 0.5 mm Wide Notch Depth (mm) |
|---|---|---|---|
| 1 | 1.5 | | |
| 2 | 1.25 | | |
| 3 | 1.0 | | |
| 4 | 0.75 | | |
| 5 | 0.5 | | |
| 6 | | 50 (unilateral) | |
| 7 | | 25 (unilateral) | |
| 8 | | 50 (antilateral) | |
| 9 | | 25 (antilateral) | |
| 10 | | | 0.25 |
| 11 | 0.5 | | |

EXAMPLE 4

A further test was done with the apparatus as described in Example 1 with an aluminum disc 32 mm thick and 254 mm in diameter. Flaw characterization is given in TABLE E4. Slots are 0.8 mm long by 1.25 mm wide.

Figure 8A:
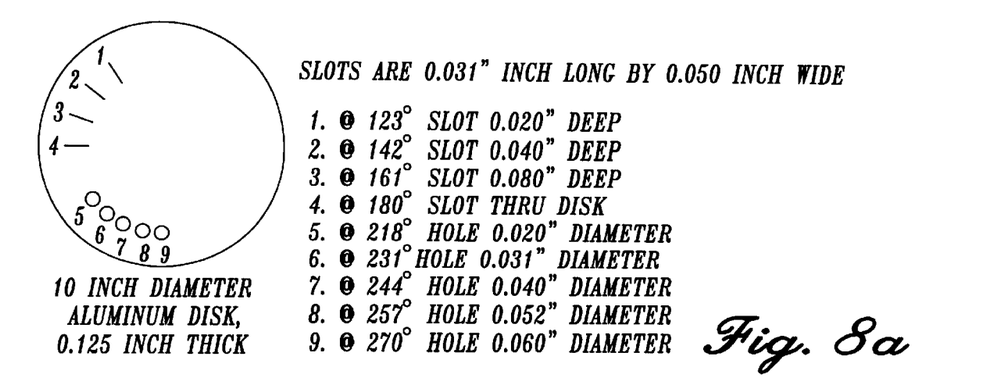
FIG. 8a is a flaw map for an aluminum disc.
Figure 8B:
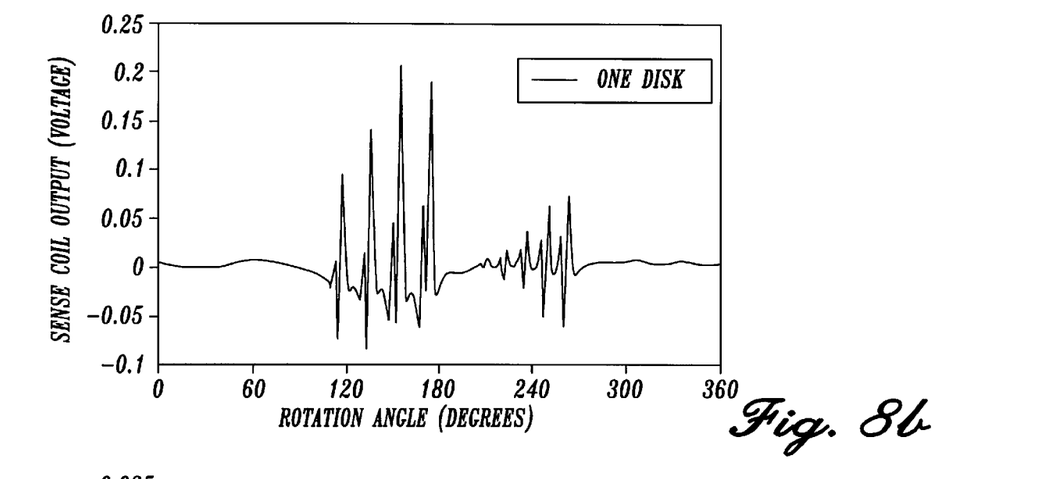
FIG. 8b is a sensor coil output for the flaws on the aluminum disc.
Figure 8C:
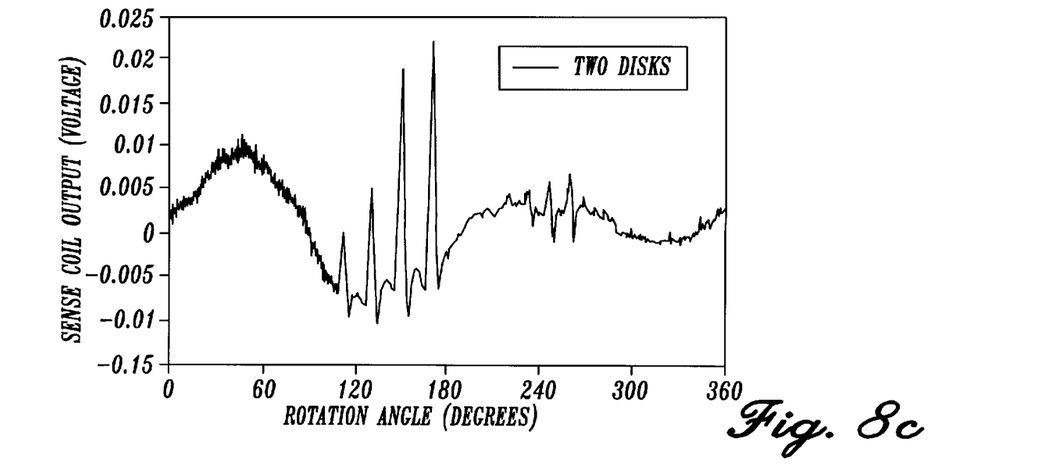
FIG. 8c is a sensor coil output for the flaws on the aluminum disc covered by a second unflawed disc, simulating a laminate.

A flaw map is shown in FIG. 8a. Sensor coil output voltages are shown in FIG. 8b. A second non-flawed disk was placed over the flawed disc to simulate a laminate having subsurface flaws. The sensor coil output voltages of the laminate are shown in FIG. 8c.

TABLE E4

Flaw Characterization

| Flaw | Position | Hole Diameter (mm) | Slot Depth (mm) |
|---|---|---|---|
| 1 | 123° | | 0.5 |
| 2 | 142° | | 1.0 |
| 3 | 161° | | 2.0 |
| 4 | 180° | | Through |
| 5 | 218° | 0.5 (through) | |
| 6 | 231° | 0.75 (through) | |
| 7 | 244° | 1.0 (through) | |
| 8 | 257° | 1.25 (through) | |
| 9 | 270° | 1.5 (through) | |

For testing the present invention and for inspection of discs, tubes or other rotating piece, a single sensing unit experiencing a plurality of passes of each flaw is sufficient to determine flaw area and/or volume. However, for inspection of sheets or non-rotating pieces, a plurality of sensing units may be used to obtain a plurality of signals from a single flaw.

PORTABLE EMBODIMENT

Figure 9:
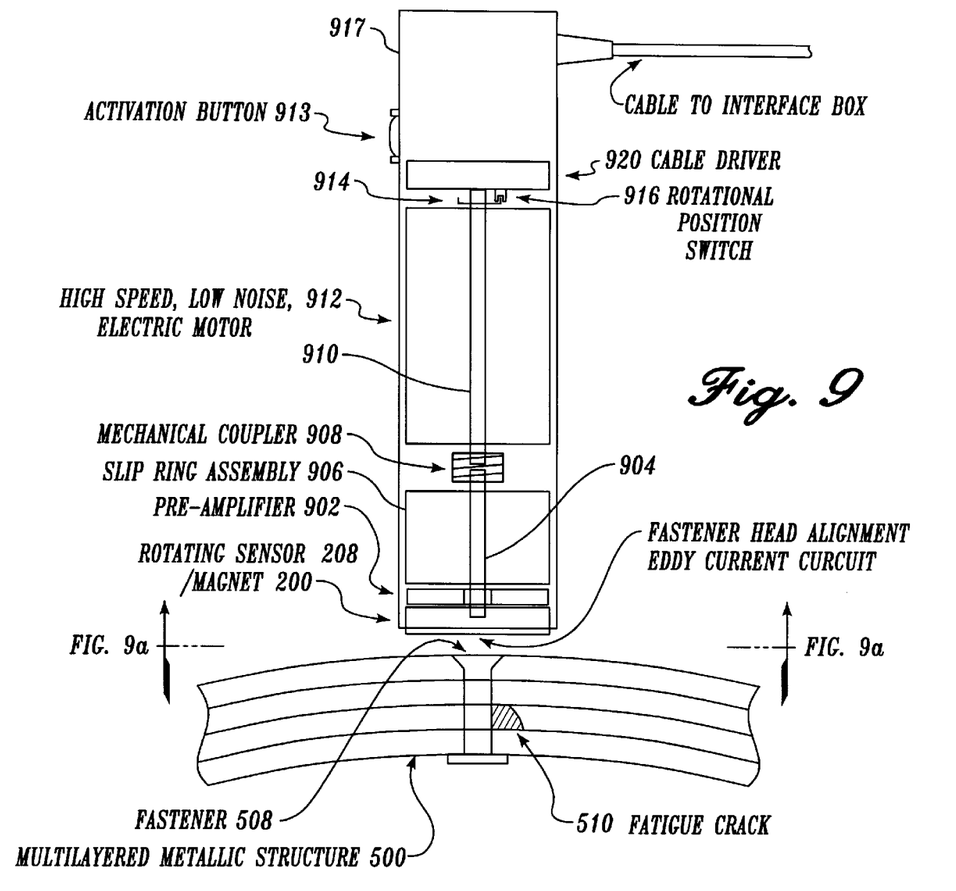
FIG. 9 is a cross section of a portable embodiment of the present invention.
Figure 9A:
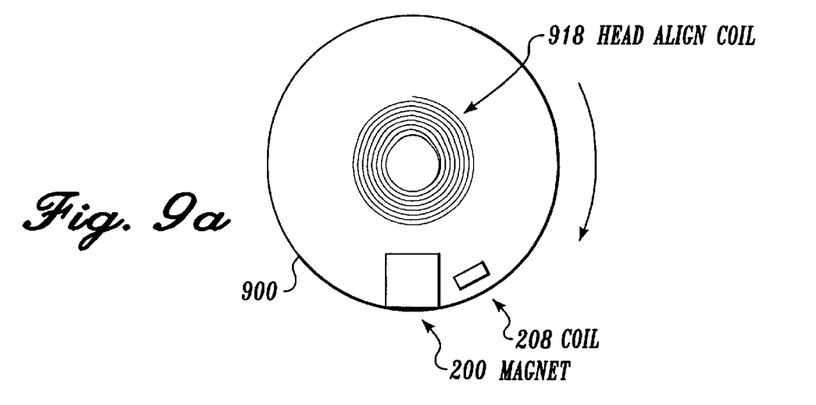
FIG. 9a is a bottom view of the portable embodiment of the present invention.

A portable embodiment of the present invention is shown in FIG. 9., FIG. 9a. The magnet 200 and sensor coil 208 are mounted eccentrically on a disk 900 in unilateral relationship. A pre-amplifier 902 is preferably mounted on the disk 900 to amplify signals from the sensor coil 208. The disk 900 is connected to a shaft 904 though a slip ring 906 into a mechanical coupler 908. The slip ring 906 permits transferring signals from the rotating sensor coil 208 to a stationary data collection device (not shown). A second shaft 910 is connected to the mechanical coupler 908 into a motor 912, preferably a high speed (up to about 500 rps), low noise electric motor. An activation button 913 is provided to operate the motor 912. The mechanical coupler 908 may be any coupler, but is preferably a flexible coupler. A second end 914 of second shaft 910 may be connected to a rotational position switch 916 used to correlate the sensor coil 208 signal with angular position. These components are preferably mounted in a housing 917.

In a preferred embodiment, an eddy current coil 918 is centrally mounted on the disk 900, specifically on the same side of the disk 900 as the magnet 200 and sensor coil 208 facing the multilayered metallic structure 500. The eddy current coil is used to sense a rivet or fastener 508 so that an operator knows when the portable embodiment is positioned over the fastener 508. The eddy current coil 918 may be attached to a light (not shown).

Further in a preferred embodiment, a cable driver 920 is used for impedance matching and signal noise reduction. A cable 922 provides power to the motor 912 and data signals to the data collection device.

Figure 10A:
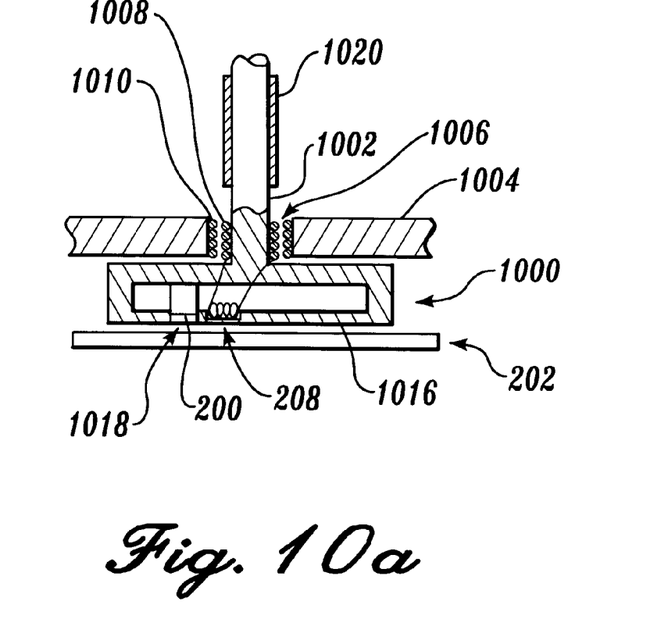
FIG. 10a is a cross section of a portable embodiment using a bobbin type dynamic transformer for signal transfer.
Figure 10B:
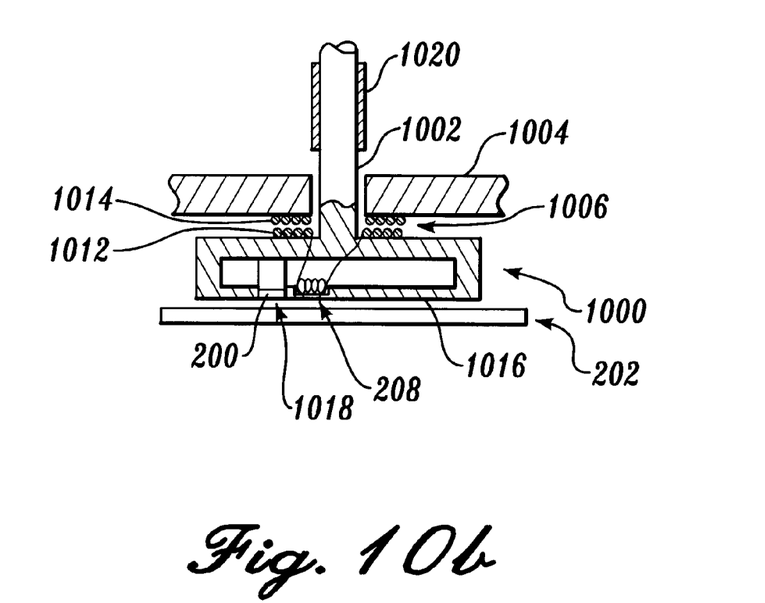
FIG. 10b is a cross section of a portable embodiment using a horizontal type dynamic transformer for signal transfer.

As an alternative to slip rings, as a signal transferrer, a dynamic transformer may be used. A dynamic transformer is similar to a static transformer inasmuch as there is no exchange of electrical energy for work, but is different because the transformer coils are in relative motion. Embodiments using dynamic transformers are shown in FIG. 10*a* and FIG. 10*b*. The magnet 200 and sensor coil 208 are mounted on a rotating disk 1000. The shaft 1002 of the rotating disk 1000 extends through a housing 1004. In FIG. 10*a* the dynamic coil 1006 is a bobbin type having an inner coil 1008 on the shaft 1002 that fits within an outer coil 1010 on the housing 1004. In order to isolate the inner coil 1008 from mechanical shaft loads, the inner coil may be wound on a split bobbin (not shown) that fits onto the shaft. In FIG. 10*b*, the dynamic coil 1006 is a horizontal type with a first flat coil 1012 on the disk 1000 and a second flat coil 1014 on the housing 1004. The first flat coil 1012 faces the second flat coil 1014. A disk cover 1016 (FIG. 10*a*) may be used to hold the sensor coil 208 independently of the magnet 200. Preferably, the disk cover 1016 has a hole 1018 permitting the magnet 200 to "see" the conductive material 202. In either embodiment, the coil wire diameter may range from 0.001 to 0.020 inch, number of turns may range from 600 to 100, and the number of layers may range from 1 to 5. The bobbin type is preferred (FIG. 10*a*) because it improves signal strength by a factor of 2 compared to the horizontal type (FIG. 10*b*). When an AC motor is used to turn the shaft 1002, it was found that coating the shaft 1002 with a polymer coating (polytetrafluoroethylene) 1020 eliminated or reduced noise from shaft surface charge. A band pass filter is recommended to reduce noise induced in the coil half that is in relative motion with respect to the magnet 200. Use of a DC motor or air driven motor may further reduce or eliminate signal noise from the motor.

CLOSURE

The data acquisition system may be used to make raster images of the conductive material showing location and severity of inclusions.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for detecting flaws in conductive material having a material surface, the apparatus is a sensing unit having (a) a magnet having a substantially constant magnetic field with a pole, the magnet placed adjacent to one side of the conductive material, with the pole facing the material surface;
   (b) a sensor coil that is unilateral and stationary with respect to the magnet wherein the magnet and sensor coil are in relative motion with respect to a conductive material, said sensor coil having a longitudinal axis; and
   (c) a signal transferrer for data acquisition; wherein the improvement comprises:
      (i) the sensor coil is positioned within a pattern of a secondary magnetic field and away from the magnet;
      (ii) said relative motion is oscillatory motion of the magnet and the sensor coil while the conductive material is stationary;
      (iii) said signal transferrer is selected from the group consisting of slip ring, inductive coupling, and radiofrequency transmitter; and
      (iv) a liftoff compensator that measures a liftoff distance between the material surface of the conductive material and the magnet.

2. The apparatus as recited in claim 1, wherein said magnet is a flat magnet.

3. The apparatus as recited in claim 1, wherein said sensor coil is oriented with its longitudinal axis parallel to said conductive material.

4. The apparatus as recited in claim 1, wherein said sensor coil is tilted.

5. The apparatus as recited in claim 1, wherein said flaw passes said sensor coil a plurality of times.

6. The apparatus as recited in claim 1, wherein said flaw passes a plurality of sensor coils.

7. The apparatus as recited in claim 1, wherein said magnet and said sensor coil are mounted eccentrically on a rotating disk and said oscillatory motion is substantially circular.

8. The apparatus as recited in claim 1, wherein said inductive coupling is a dynamic transformer having a first coil and a second coil, the first coil mounted on the rotating disk and thereby stationary in relation to the magnet and sensor coil and connected to the sensor coil, the second coil mounted on a rotator housing with a gap between the first coil and the second coil.

9. The apparatus as recited in claim 8, wherein the dynamic transformer is a horizontal type.

10. The apparatus as recited in claim 8, wherein the dynamic transformer is a bobbin type.

11. The apparatus as recited in claim 7, further comprising an eddy current coil for sensing a fastener.

12. The apparatus as recited in claim 7, further comprising a rotational position switch for correlating signals from the rotating sensor coil with angular position of the rotating sensor coil.

13. The apparatus as recited in claim 1, wherein the oscillatory motion is achieved by vibration.

14. A method for detecting flaws in conductive material having a material surface, the method having the steps of:

(a) providing a sensing unit having a magnet having a substantially constant magnetic field with a pole, placing the magnet adjacent to one side of the conductive material with the pole facing the conductive material;
   (b) providing a sensor coil that is unilateral and stationary with respect to the magnet wherein the magnet and sensor coil are in relative motion with respect to the conductive material, said sensor coil having a longitudinal axis; and (c) transferring a signal from the sensor coil to a data acquisition system; wherein the improvement comprises:
  (i) positioning the sensor coil within a circular pattern of a secondary magnetic field and away from the magnet;
  (ii) oscillating the magnet and the sensor coil while the conductive material is stationary;
  (iii) selecting said signal transferrer from the group consisting of slip ring, inductive coupling, and radiofrequency transmitter; and
  (iv) measuring a liftoff distance between the material surface of the conductive material and the magnet.

15. The method as recited in claim 14, wherein said magnet is a flat magnet.

16. The method as recited in claim 14, wherein said sensor coil is oriented with its longitudinal axis parallel to said conductive material.

17. The method as recited in claim 14, wherein said sensor coil is tilted.

18. The method as recited in claim 14, further comprising the step of passing said flaw past said sensor coil a plurality of times.

19. The method as recited in claim 14, wherein said sensing unit has a plurality of sensor coils for a single magnet.

20. The method as recited in claim 14, further comprising the step of making a contour plot of said flaw.

21. The method as recited in claim 14, wherein transferring the signal is by dynamically transforming with a dynamic transformer having a first coil and a second coil, the first coil mounted on the rotating disk and thereby stationary in relation to the magnet and sensor coil and connected to the sensor coil, the second coil mounted on a rotator housing with a gap between the first coil and the second coil.

22. The method as recited in claim 21, wherein the dynamic transformer is a horizontal type.

23. The apparatus as recited in claim 21, wherein the dynamic transformer is a bobbin type.

24. An apparatus for detecting flaws in conductive material having a material surface, the apparatus is a sensing unit having
  (a) a magnet having a substantially constant magnetic field with a pole, the magnet placed adjacent to one side of the conductive material, with the pole facing the material surface;
  (b) a sensor coil that is unilateral and stationary with respect to the magnet wherein the magnet and sensor coil are in relative motion with respect to a conductive material, said sensor coil having a longitudinal axis; and
  (c) a signal transferrer for data acquisition; wherein the improvement comprises:
    (i) the sensor coil is positioned within a circular pattern of a secondary magnetic field and spaced apart from the magnet at a spacine that is less than one magnet dimensions;
    (ii) said relative motion is oscillatory motion of the magnet and the sensor coil while the conductive material is stationary; and
    (iii) said signal transferrer is an inductive coupling.

25. The apparatus as recited in claim 24, further comprising a liftoff compensator that measures a liftoff distance between the material surface of the conductive material and the magnet.

26. The apparatus as recited in claim 24, wherein said inductive coupling is a dynamic transformer having a first coil and a second coil, the first coil mounted on the rotating disk and thereby stationary in relation to the magnet and sensor coil and connected to the sensor coil, the second coil mounted on a rotator housing with a gap between the first coil and the second coil.

27. The apparatus as recited in claim 26, wherein the dynamic transformer is a horizontal type.

28. The apparatus as recited in claim 26, wherein the dynamic transformer is a bobbin type.

* * * * *